US009309183B2

United States Patent
Storzum et al.

(10) Patent No.: US 9,309,183 B2
(45) Date of Patent: Apr. 12, 2016

(54) PLASTICIZER COMPOSITION COMPRISING DI(2-ETHYLHEXYL) TEREPHTHALATE

(71) Applicant: BASF SE, Ludwigshafen (DE)

(72) Inventors: Uwe Storzum, League City, TX (US); Boris Breitscheidel, Waldsee (DE); Kevin Scott Todd, Lake Jackson, TX (US); Jason David Veinot, Ontario (CA)

(73) Assignee: BASF CORPORATION, Florham Park, NJ (US)

( * ) Notice: Subject to any disclaimer, the term of this patent is extended or adjusted under 35 U.S.C. 154(b) by 99 days.

(21) Appl. No.: 14/184,853

(22) Filed: Feb. 20, 2014

(65) Prior Publication Data

US 2015/0232411 A1    Aug. 20, 2015

(51) Int. Cl.

| | |
|---|---|
| C08F 236/12 | (2006.01) |
| C08L 33/06 | (2006.01) |
| C09B 67/00 | (2006.01) |
| C07C 69/76 | (2006.01) |
| C07C 67/08 | (2006.01) |
| C08K 5/12 | (2006.01) |

(52) U.S. Cl.
CPC .. *C07C 67/08* (2013.01); *C08K 5/12* (2013.01)

(58) Field of Classification Search
None
See application file for complete search history.

(56) References Cited

U.S. PATENT DOCUMENTS

| | | | | |
|---|---|---|---|---|
| 6,548,109 | B1 * | 4/2003 | Hagquist et al. | 427/195 |
| 7,799,942 | B2 | 9/2010 | Osborne et al. | |
| 2003/0014948 | A1 * | 1/2003 | Gott et al. | 53/461 |
| 2007/0038001 | A1 | 2/2007 | Cook et al. | |
| 2007/0161815 | A1 * | 7/2007 | Osborne et al. | 560/76 |
| 2012/0174404 | A1 | 7/2012 | Wolz | |
| 2012/0202725 | A1 | 8/2012 | Grass et al. | |
| 2013/0310472 | A1 | 11/2013 | Becker et al. | |
| 2013/0331491 | A1 | 12/2013 | Becker et al. | |
| 2014/0024754 | A1 | 1/2014 | Becker et al. | |

FOREIGN PATENT DOCUMENTS

| | | |
|---|---|---|
| CA | 2 817 803 A1 | 5/2012 |
| JP | 2007-077042 A | 3/2007 |
| WO | WO 03/002640 A1 | 1/2003 |
| WO | WO 2010/071717 A1 | 6/2010 |
| WO | WO 2011/023490 A1 | 3/2011 |
| WO | WO 2011/023491 A1 | 3/2011 |
| WO | WO 2012/069287 A1 | 5/2012 |
| WO | WO 2012/113608 A1 | 8/2012 |
| WO | WO 2012/113609 A1 | 8/2012 |

OTHER PUBLICATIONS

English language abstract for WO 2011/023490 extracted from espacenet.com database on Jul. 31, 2014, 1 page.
English language abstract for WO 2011/023491 extracted from espacenet.com database on Jul. 31, 2014, 1 page.
English language abstract for WO 2012/069287 extracted from espacenet.com database on Jul. 31, 2014, 1 page.
English language abstract for WO 2012/113608 extracted from espacenet.com database on Jul. 31, 2014, 1 page.
English language abstract for WO 2012/113609 extracted from espacenet.com database on Jul. 31, 2014, 1 page.
Eastman Chemical Company, "A Comparison of Eastman 168 Plasticizer With Palatinol 79P and Eastman DOP Plasticizers," Publication L-216D, Jun. 2003.
Eastman Chemical Company, "Eastman 425 Plasticizer (Non-Orthophthalate)," Publication L-227A, Mar. 2001.
Eastman Chemical Company, "Eastman Plasticizers Selector Chart", Publication L-174L, Jun. 2002.
Eastman Chemical Company, "Safety Data Sheet", 2012, pp. 1-11.
Cooper, Ph.D., James L., "An Alternative to DEHP in Plasticized PVC", Eastman Chemical Company, Mar. 2005, pp. 1-18.
International Search Report for Application No. PCT/US2014/017261 dated Nov. 13, 2014, 3 pages.
English language abstract and machine-assisted English translation for JP 2007-077042 extracted from the PAJ database on Nov. 24, 2014, 26 pages.

* cited by examiner

*Primary Examiner* — Susannah Chung
*Assistant Examiner* — Robert T Butcher
(74) *Attorney, Agent, or Firm* — Howard & Howard Attorneys PLLC

(57) ABSTRACT

A plasticizer composition is disclosed that includes di(2-ethylhexyl) terephthalate, and which is substantially free of a di-ester according to Formula I:

Formula I $$R_1-O-C(=O)-C_6H_4-C(=O)-O-CH_2-CH(C_2H_5)-CH_2-CH_2-CH_2-CH_3$$

where $R_1$ is a straight-chain or branched alkyl group having from 1 to 13 carbon atoms, and where $R_1$ is different than 2-ethylhexane. The plasticizer composition may be used in a plastisol composition, a powder coating composition, a molding composition, and various other compositions. A method of preparing an aromatic di-ester is also disclosed. The method may prepare the plasticizer composition.

44 Claims, No Drawings

PLASTICIZER COMPOSITION COMPRISING DI(2-ETHYLHEXYL) TEREPHTHALATE

FIELD OF THE INVENTION

The present disclosure generally relates to a plasticizer composition that includes di(2-ethylhexyl) terephthalate (DOTP), and which is substantially free of impurities, and a method for preparing the same.

BACKGROUND

Conventional plasticizer compositions that include (DOTP) also include an influential amount of impurities or byproducts that restrict or preclude certain applications of the conventional plasticizer composition.

Conventional plasticizer compositions are prepared by conventional methods. Typically during the conventional methods, DOTP is prepared by reacting 2-ethylhexanol and terephthalic acid in the presence of a catalyst. Certain reaction conditions used in the conventional methods have a tendency to decompose the 2-ethylhexanol and/or the titanium catalyst to form a variety of decomposition products. These decomposition products subsequently react with terephthalic acid to produce the impurities. Typically, the impurities include a di-ester according to Formula I:

Formula I

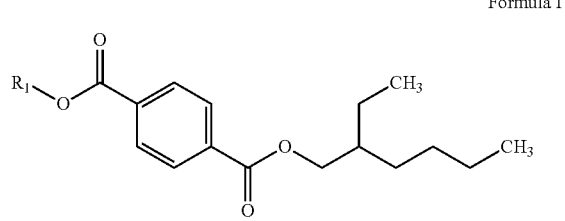

where $R_1$ is a straight-chain or branched alkyl group having from 1 to 13 carbon atoms, and $R_1$ is different than 2-ethylhexane One of the most prevalent and influential impurities is methyl(2-ethylhexyl) terephthalate (MOTP). Conventional plasticizer compositions include the di-ester according to Formula I in an amount greater than 0.1 parts by weight based on 100 parts by weight of the conventional plasticizer composition. Typically, the conventional plasticizer composition includes the di-ester according to Formula I in an amount greater than 1, 1.5, or 2, parts by weight based on 100 parts by weight of the conventional plasticizer composition.

In addition to the di-ester according to Formula I, conventional plasticizers typically also include other impurities formed from the reaction product of (1) terephthalic acid and (2) decomposition products of 2-ethylhexanol and/or decomposition products of the titanium catalyst.

These impurities are chemically similar to DOTP and, as such, cannot be removed through conventional separation techniques (e.g. washing, filtering, distilling, etc.). As such, these impurities, especially MOTP, result in increased volatility and fogging of the conventional plasticizer composition and articles, films, or compositions containing the conventional plasticizer composition. As such, the presence of the impurities contained within the conventional plasticizer composition restrict or preclude the use of the conventional plasticizer composition in a variety of articles, films, and various other compositions. Accordingly, there remains an opportunity to develop an improved plasticizer composition.

SUMMARY OF THE INVENTION AND ADVANTAGES

The present disclosure provides a plasticizer composition which comprises di(2-ethylhexyl) terephthalate (DOTP), and which is substantially free of a di-ester according to Formula I:

Formula I

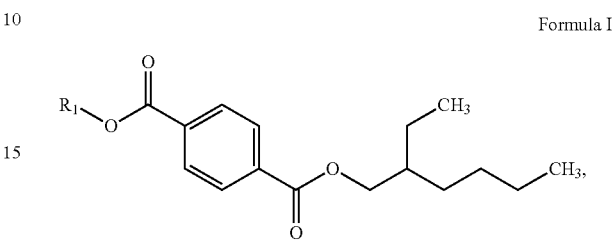

where $R_1$ is a straight-chain or branched alkyl group having from 1 to 13 carbon atoms, and $R_1$ is different than 2-ethylhexane.

The present disclosure also provides a method for preparing an aromatic di-ester. The method includes the step of combining an aromatic di-ester and a linear or branched C4-C13 alcohol to form a mixture. The method also includes heating the mixture from a first temperature (T1) to a second temperature (T2) without a catalyst present in the mixture. The method also includes combining a titanium catalyst with the mixture after the mixture is at the second temperature (T2). The method further includes increasing pressure from a first pressure (P1) to a second pressure (P2) after the mixture is at the second temperature (T2), and increasing the temperature from the second temperature (T2) to a third temperature (T3) while maintaining the second pressure (P2).

Unlike conventional plasticizer compositions that include DOTP, the plasticizer composition of this disclosure is substantially free of a di-ester according to Formula I. As such, the plasticizer composition of this disclosure has a lower volatility than a conventional plasticizer compositions. As a result of this lower volatility, articles, films, or other compositions that include the plasticizer composition of this disclosure have good fogging behavior, which is important for the use and durability of the articles, films, and/or compositions.

DETAILED DESCRIPTION OF THE INVENTION

Plasticizer compositions are typically used to obtain desirable processing and application properties in many polymers to make them softer, more flexible and/or more extensible. In general, plasticizer compositions lower a glass transition temperature of the polymer to reach desired elastic properties at lower processing and application temperatures.

Polyvinyl chloride (PVC) is among the most widely produced polymers used in forming plastics. Owing to its great versatility, PVC is found in numerous products used in daily life. PVC is therefore of enormous economic importance. However, PVC in its original state (i.e., PVC without a plasticizer composition) is hard and brittle below temperatures of 80° C. As such, incorporating a plasticizer composition into PVC is essential.

Examples of other significant polymers in which plasticizer compositions are typically used are polyvinyl butyral (PVB), homo- and copolymers of styrene, polyacrylate, polyvinyl acetate (PVAc), cellulose acetate (CA), polysulfide and thermoplastic polyurethane (TPU).

The present disclosure provides a plasticizer composition which comprises di(2-ethylhexyl) terephthalate (DOTP), and which is substantially free of a di-ester according to Formula I:

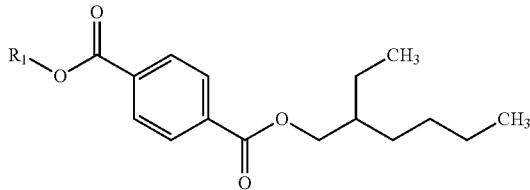

Formula I where $R_1$ is a straight-chain or branched alkyl group having from 1 to 13 carbon atoms, and $R_1$ is different than 2-ethylhexane.

Substantially free in the context of this disclosure provides that the plasticizer composition includes the di-ester according to Formula I in an amount of from about 0.1 to 0, from about 0.07 to 0, from about 0.05 to 0, from about 0.03 to 0, or from about 0.01 to 0, parts by weight based on 100 parts by weight of the plasticizer composition. In certain embodiments, the plasticizer composition is completely free of (i.e., does not include) the di-ester according to Formula I.

DOTP is the reaction product of two moles of 2-ethylhexanol and one mole of terephthalic acid. Typically, the reaction takes place in the presence of a catalyst such as a titanium catalyst. The structure of DOTP is provided in Formula II.

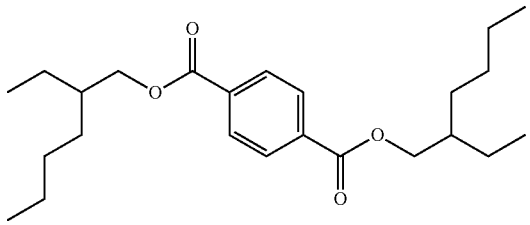

Formula II

DOTP is formed when the two moles of 2-ethylhexanol reacts with the two moles of carboxylic acid functionality that is present in the terephthalic acid. Typically, excess 2-ethylhexanol is used to ensure conversion of the terephthalic acid. Although the reaction scheme to prepare DOTP appears to be relatively straight forward, conventional methods of preparing DOTP result in an influential amount of the di-ester according to Formula I.

When present, the di-ester according to Formula I is produced during the reaction that prepares DOTP. In other words, the di-ester according to Formula I is an impurity/byproduct derived from the DOTP reaction. Without being held to any particular theory, it is believed that the reaction conditions (or pairing of reaction conditions) used to prepare DOTP are sufficient to decompose the 2-ethylhexanol and/or the titanium catalyst into a variety of decomposition products which subsequently react with one mole of the carboxylic acid on the terephthalic acid and ultimately produce (after an undecomposed mole of 2-ethylhexanol also reacts with the same mole of terephthalic acid) the di-ester according to Formula I. Conventional plasticizer compositions are prepared from conventional methods that form an influential amount of the di-ester according to Formula I. Conversely, the plasticizer composition of this disclosure includes DOTP, and is substantially free of the di-ester according to Formula I. In other words, the method of preparing the plasticizer composition of this disclosure limits, and in certain embodiments eliminates, the decomposition of 2-ethylhexanol and thus prepares the plasticizer composition is substantially free of the di-ester according to Formula I. The method for preparing the plasticizer composition of this disclosure is described in detail below.

Referring back to the di-ester according to Formula I, examples of $R_1$ include methane, ethane, n-propane, isopropane, n-butane, isobutane, n-pentane, isopentane, n-hexane, isohexane, n-heptane, isoheptane, n-octane, isooctane, n-nonane, isononane, n-decane, isodecane, n-undecane, isoundecane, n-dodecane, isododecane, n-tridecane and isotridecane. Typically $R_1$ is methane, and consequently the di-ester according to Formula I includes MOTP.

As briefly described above, the titanium catalyst may also decompose under certain reaction conditions (or pairing of reaction conditions) used to prepare DOTP. However, even though the plasticizer composition of this disclosure is prepared from a method that typically uses a titanium catalyst, in certain embodiments, the plasticizer composition of this disclosure is also substantially free of the reaction product formed from terephthalic acid and the decomposition products of the titanium catalyst. In other words, in certain embodiments, the titanium catalyst does not decompose.

In certain embodiments, the plasticizer composition is substantially free of the reaction product of (1) terephthalic acid and (2) decomposition products of 2-ethylhexanol, decomposition products of a titanium catalysts, or combinations thereof.

In certain embodiments, the plasticizer composition is also substantially free of di(methyl) terephthalate (DMT). Although the source of DMT may vary, DMT is typically formed when a large amount of 2-ethylhexanol and/or the catalyst decomposes so that two moles of the decomposition products react with one mole of terephthalic acid. In other embodiments, the plasticizer composition is substantially free of DMT and substantially free of the reaction product of (1) terephthalic acid and (2) decomposition products of 2-ethylhexanol, decomposition products of a titanium catalysts, or combinations thereof.

In certain embodiments, the plasticizer composition is substantially free of every reaction product formed from the reaction between (1) terephthalic acid and (2) the decomposition products of 2-ethylhexanol and/or the decomposition product of the titanium catalyst. In other words, to the extent that the reaction product of (1) terephthalic acid and (2) the decomposition products of 2-ethylhexanol and/or the decomposition products of the titanium catalyst is not represented by Formula I, the plasticizer composition is also substantially free of those reaction products not expressed by Formula I and formed from the reaction product of (1) terephthalic acid and (2) the decomposition products of 2-ethylhexanol and/or the decomposition products of the titanium catalyst. It is to be appreciated that avoiding these impurities is also advantageous because in theory these impurities could also adversely impact the performance and/or appearance of the plasticizer composition.

In certain embodiments, the plasticizer composition includes DOTP in an amount of from about 85 to about 99.8, from about 90 to about 99.8, from about 95 to about 99.8 or from about 97 to about 99, parts by weight based on 100 parts by weight of the plasticizer composition. In these embodiments, the di-ester according to Formula I is present in an amount of from about 0.1 to 0, from about 0.05 to 0, or from about 0.03 to 0, parts by weight based on 100 parts by weight of the plasticizer composition.

In certain embodiments, the plasticizer composition includes DOTP in an amount greater than or equal to 99.9 parts by weight based on 100 parts by weight of the plasticizer composition. As such, in this embodiment, the di-ester according to Formula I is present in an amount less than 0.1 parts by weight based on 100 parts by weight of the plasticizer composition.

In certain embodiments, the plasticizer composition includes DOTP in an amount greater than or equal to 99.95 parts by weight based on 100 parts by weight of the plasticizer composition. As such, in this embodiment, the di-ester according to Formula I is present in an amount less than 0.05 parts by weight based on 100 parts by weight of the plasticizer composition.

In certain embodiments, the plasticizer composition includes DOTP in an amount greater than or equal to 99.97 parts by weight based on 100 parts by weight of the plasticizer composition. As such, in this embodiment, the di-ester according to Formula I is present in an amount less than 0.03 parts by weight based on 100 parts by weight of said plasticizer composition.

The di-ester according to Formula I is volatile. Because the presence of the di-ester according to Formula I increases the volatility of any plasticizer composition that includes the di-ester according to Formula I, the plasticizer composition of this disclosure has a lower volatility than conventional plasticizer compositions due to the fact that conventional plasticizer compositions include an influential amount of the di-ester according to Formula I and the plasticizer composition of this disclosure is substantially free of the di-ester according to Formula I.

In general, the lower the volatility of a particular plasticizer composition, the lower the fogging value of that plasticizer composition or an article that includes that particular plasticizer composition. The fogging value is generally understood as a tendency of a material (e.g. plasticized PVC) to produce a light scattering film (i.e., "a fog") on a glass surface. When the material includes a particular plasticizer composition, the plasticizer composition largely affects the fogging value despite the fact that the concentration of the plasticizer composition in the material is generally low. In other words, the lower the volatility of a plasticizer composition, the lower the fogging value of a material that includes the plasticizer composition. As such, the plasticizer composition of this disclosure is superior to conventional plasticizer compositions in respect to volatility and fogging. It is to be appreciated that even small decreases (e.g. 0.02%) in the amount of the di-ester according to Formula I is significant because the decrease in the di-ester according to Formula I is typically directly correlated to a decrease in the fogging value. As such, because the plasticizer composition of this disclosure include a lesser amount of the di-ester according to Formula I than that of the conventional plasticizer compositions, the plasticizer composition of this disclosure also has a lower fogging value than conventional plasticizer compositions.

The plasticizer composition also has a high degree of compatibility with a large number of different plasticizers. In fact, the plasticizer composition can be advantageously combined with other plasticizers to improve the properties (e.g. gelling) of the other plasticizers. As such, in certain embodiments, the plasticizer composition further includes an additional plasticizer that is different from DOTP and is different from the di-ester according to Formula I. Typically, the additional plasticizer is one or more esters selected from a group consisting of cyclohexanedicarboxylic acid esters, phthalic acid dialkyl esters, phthalic acid alkylaralkyl esters, terephthalic acid dialkyl esters that are different from the di-ester according to Formula I and different from di(methyl) terephthalate, trimellitic acid trialkyl esters, adipic acid dialkyl esters, benzoic acid alkyl esters, dibenzoic acid esters of glycols, hydroxybenzoic acid esters, esters of saturated monocarboxylic acids and dicarboxylic acids, esters of unsaturated dicarboxylic acids, esters of amides, esters of aromatic sulfonic acids, alkylsulfonic acid esters, glycerol esters, isosorbide esters, phosphoric acid esters, citric acid triesters, alkylpyrrolidone derivatives, 2,5-furandicarboxylic acid esters, 2,5-tetrahydrofurandicarboxylic acid esters, epoxidized vegetable oils based on triglycerides and saturated or unsaturated fatty acids, and polyesters of aliphatic and aromatic polycarboxylic acids with polyhydric alcohols.

In embodiments where the plasticizer composition contains the additional plasticizer, the plasticizer composition is still substantially free of the di-ester according to Formula I. However, in this context, the amount of the di-ester according to Formula I is based on 100 parts by weight of the plasticizer composition without taking into consideration the additional plasticizer component. For example, if the plasticizer composition includes 98 parts by weight of DOTP, 1.95 parts by weight of the additional plasticizer, and 0.05 parts by weight of the di-ester according to Formula I, for the purposes of calculating the amount of the at least di-ester according to Formula I, the 100 parts by weight of the plasticizer composition should be normalized to account for only the DOTP and the di-ester according to Formula I. In other words, the inclusion of the additional plasticizer is not intended to be a diluting medium for decreasing the amount of the di-ester according to Formula I by simply increasing the number of components in the plasticizer composition.

Referring back to the one or more esters, In certain embodiments, the cyclohexanedicarboxylic acid esters have 4 to 13 carbon atoms or 8 to 10 carbon atoms, independently in each alkyl chain. In certain embodiments, the cyclohexane-dicarboxylic acid esters are 1,2-cyclohexanedicarboxylic acid esters that have 8 to 10 carbon atoms independently in each alkyl chain. In one embodiment, the 1,2-cyclohexane-dicarboxylic acid diisononyl ester, which is supplied by BASF SE, Ludwigshafen, under the trade name HEXAMOLL® DINCH®. In certain embodiments, the phthalic acid dialkyl esters have 4 to 13 carbon atoms or 8 to 13 carbon atoms, independently in each alkyl chain. In one embodiment, the phthalic acid alkylaralkyl ester is, for example, benzylbutyl phthalate. In certain embodiments, the terephthalic acid dialkyl esters have 4 to 13 carbon atoms or 4 to 10 carbon atoms, independently in each alkyl chain. In certain embodiments, the terephthalic acid dialkyl esters are di(n-butyl) terephthalic acid dialkyl ester, di(isononyl)-terephthalic acid dialkyl ester and/or di(2-propylheptyl)terephthalic acid dialkyl ester. The trimellitic acid trialkyl esters typically have 4 to 13 carbon atoms or 7 to 11 carbon atoms, independently in each alkyl chain. In certain embodiments, the esters of saturated mono and dicarboxylic acid are esters of acetic acid, butyric acid, valeric acid, succinic acid, adipic acid, sebacic acid, lactic acid or tartaric acid. The adipic acid dialkyl esters typically have 4 to 13 carbon atoms or 6 to 10 carbon atoms, independently in each alkyl chain. In certain embodiments, the adipic acid dialkylesters are di(2-ethylhexyl)adipate and/or diisononyladipate. The esters of unsaturated dicarboxylic acids are typically esters of maleic acid and/or fumaric acid. Typically, the benzoic acid alkyl esters have 7 to 13 carbon atoms or 9 to 13 carbon atoms, independently in each alkyl chain. In certain embodiments, the benzoic acid alkyl esters are isononyl benzoate, isodecyl benzoate and/or 2-propylheptyl benzoate. In certain embodiments, the dibenzoic acid esters of glycols are diethylene glycol dibenzoate and dibutylene glycol dibenzoate. In certain embodiments, the alkylsulfonic acid esters have an alkyl group of 8 to 22 carbon atoms. Examples include the phenyl and cresyl esters of pentadecylsulfonic acid. In one embodiment, the isosorbide esters are isosorbide diesters that are each independently esterified with C5 to C13 carboxylic acids. Typically the phosphoric acid esters are tri-2-ethylhexyl phosphate, trioctyl phosphate, triphenyl phosphate, isodecyldiphenyl phosphate, 2-ethylhexyl-diphenyl phosphate and bis-(2-ethylhexyl)phenyl phosphate. In the citric acid triesters, the hydroxyl group may be present in free or carboxylated, or acetylated, form. The alkyl groups of the citric acid triesters typically each independently have 4 to 8 carbon atoms or 6 to 8 carbon atoms. In certain embodiments, the alkylpyrrolidone derivatives are those with alkyl groups of 4 to 18 carbon atoms. In one embodiment, the 2,5-furandicarboxylic acid dialkyl esters have 4 to 13 carbon atoms or 8 to 13 carbon atoms, independently in each alkyl chain. In certain embodiments, the epoxidized vegetable oils are, for example, epoxidized fatty acid esters composed of epoxidized soybean oil and/or epoxidized tall oil fatty acids (reacted with alcohols of chain-length 1 to 8 carbon atoms), supplied under the trade name REFLEX® by PolyOne, USA, under the trade names PROVIPLAST® PLS GREEN 5 and PROVIPLAST® PLS GREEN 8 by Proviron, Belgium, and under the trade name DRAPEX®, DRAPEX ALPHA by Galata, USA. The polyesters of aliphatic and aromatic polycarboxylic acids are typically polyesters of adipic acid with polyhydric alcohols, in particular dialkylene glycol polyadipate with 2 to 6 carbon atoms in the alkylene group. In all the above described esters, and those esters described herein, the alkyl groups may be linear or branched and either identical or different.

In one embodiment, the one or more esters is an adipic acid dialkyl esters with 4 to 9 carbon atoms in the alkyl group. In another embodiment, the one or more esters is one or more C5 to C11 or C7 to C10 dialkyl ester of 2,5-furandicarboxylic acid. In one embodiment, the C5 to C11 dialkyl ester of 2,5-furandicarboxylic acid is the di(2-ethylhexyl)-ester of 2,5-furandicarboxylic acid.

The dialkyl esters of 2,5-furandicarboxylic acid are described in WO 2012/113608 (C5 dialkyl esters), WO 2012/113609 (C7 dialkyl esters), WO 2011/023490 (C9 dialkyl esters) and WO 2011/023491 (C10 dialkyl esters). The dihexyl-, di(2-ethylhexyl)- and di(2-octyl)-esters of 2,5-furandicarboxylic acid and their manufacture are described by R. D. Sanderson et al. in J. Appl. Pol. Sci., 1994, Vol. 53, 1785-1793. The disclosure of these publications is incorporated by reference in their entirety.

In certain embodiments, the dialkyl esters of 2,5-furandicarboxylic acid are the isomeric nonyl esters of 2,5-furandicarboxylic acid described in WO 2011/023490. The isomeric nonyl groups may be derived from a mixture of isomeric nonanols, as described in WO 2011/023490, page 6, line 32, to page 10, line 15.

In one embodiment, the additional plasticizer is selected from the group of C4 to C5 dialkyl esters of 2,5-tetrahydrofuran dicarboxylic acid and the C4 to C5 dialkyl ester derivatives of 2,5-di(hydroxymethyl)tetrahydrofuran and 2,5-di(hydroxyethyl)tetrahydrofuran. In certain embodiments, the additional plasticizer is the C4 to C5 dialkyl esters of 2,5-tetrahydrofurandicarboxylic acid, especially di(isobutyl)-2,5-tetrahydrofuran dicarboxylate and di(n-butyl)-2,5-tetrahydrofuran dicarboxylate.

The plasticizer composition may advantageous be used to plasticize polymers, particularly where there are special or complex application-based requirements, such as high flexibility at low temperatures, high extraction and migration resistance, or very low plasticizer volatility. These complex application-based requirements are especially prevalent in PVC applications.

PVC is obtained by homopolymerization of vinyl chloride. The PVC used in the context of the present disclosure may be polymerized by suspension polymerization, micro-suspension polymerization, emulsion polymerization or mass polymerization. The manufacture of PVC by polymerization of vinyl chloride and the manufacture and composition of plasticized PVC is described, for example, in Becker and Braun, Plastics Handbook, Volume 2/1: Polyvinyl Chloride, 2nd Edition, Carl Hanser Verlag, Munich, and is hereby incorporated by reference in its entirety. Typically, PVC that includes the plasticizer composition of this disclosure has a K value, which characterizes the molar mass of the PVC and is determined according to DIN 53726, of from about 57 to about 90, from about 61 to about 85, or from about 64 to about 75.

The present disclosure also provides a molding composition comprising the plasticizer composition. The molding composition also includes one or more polymers. The polymer of the molding composition may be any polymer that is suitable for thermoplastic processing. In particular, such polymers are selected from among the following: homo and copolymers that include one or more monomer in polymerized form selected from the C2-C10 monoolefins, such as ethylene or propylene, 1,3-butadiene, 2-chloro-1,3-butadiene, vinyl alcohol and its C2-C10 alkyl esters, vinyl chloride, vinylidene chloride, vinylidene fluoride, tetrafluoroethylene, glycidyl acrylate, glycidyl methacrylate, acrylates and methacrylates with alcohol components of branched and unbranched C1-C10 alcohols, vinyl aromatic compounds such as polystyrene, (meth)acrylonitrile, ethylenic unsaturated mono and dicarboxylic acids, and maleic anhydride, homo- and copolymers of vinyl acetals, polyvinyl esters, polycarbonates (PC), polyesters such as polyalkylene terephthalates, polyhydroxyalkanoates (PHA), polybutylene succinates (PBS), polybutylene succinate adipates (PBSA), polyethers, polyamides, polyacrylonitrile, polymethyl methacrylates, polyvinylidene chloride, polystyrene (PS), polyether ketones, polyurethane (PU), thermoplastic polyurethanes (TPU), polysulfides, polysulfones, polyphenylene ether (PPE), and combinations thereof.

Examples are polyacrylates with identical or different alcohol groups selected from the C4-C8 alcohols, especially butanol, hexanol, octanol and 2-ethylhexanol, poly(methyl methacrylate) (PMMA), methyl methacrylate-butyl acrylate copolymers, acrylonitrile-butadiene-styrene copolymers (ABS), ethylene-propylene copolymers, ethylene-propylene-diene copolymers (EPDM), polystyrene (PS), styrene-acrylonitrile copolymers (SAN), acrylonitrile styrene acrylate (ASA), styrene-butadiene-methyl methacrylate copolymers (SBMMA), styrene-maleic anhydride copolymers, styrene-methacrylic acid copolymers (SMA), polyoxymethylene (POM), polyvinyl alcohol (PVAL), polyvinyl acetate (PVA), polyvinyl butyral (PVB), polycaprolactone (PCL), polyhydroxybutyric acid (PHB), polyhydroxyvaleric acid (PHV), polylactic acid (PLA), ethylcellulose (EC), cellulose acetate (CA), cellulose propionate (CP) and cellulose acetate butyrate (CAB).

Although not required, typically the polymer is PVC, polyvinyl butyral (PVB), a homo- or copolymer of vinyl acetate, a homo- or copolymer of styrene, a polyacrylate, a thermoplastic polyurethane (TPU) or a polysulfide.

The polymer contained within the molding composition may also be an elastomer. Suitable examples of the elastomer include, but are not limited to, one or more natural rubber (NR), one or more synthetic rubber or mixtures of these rubbers. In certain embodiments, the synthetic rubbers are, for example, polyisoprene rubber (IR), styrene-butadiene rubber (SBR), butadiene rubber (BR), nitrile-butadiene rubber (NBR) and chloroprene rubber (CR). In certain embodiments, the rubbers and/or rubber mixtures can be vulcanized with sulfur.

In certain embodiments, the molding composition includes the polymer in an amount of from about 20 to about 99, from about 45 to about 95, from about 50 to about 90, or from about 55 to about 85, parts by weight based on 100 parts by weight of the molding composition.

In certain embodiments, the polymer of which one or more is contained in the molding composition is PVC. In certain embodiments, the molding composition includes both PVC and the elastomer.

The molding composition may also comprise the additional plasticizer. When included, the amount of the additional plasticizer in the molding composition is from about 1 to about 90, from about 5 to about 50, or from about 10 to about 30, parts by weight based on 100 parts by weight based on the total amount of plasticizer. The total amount of plasticizer is the summation of each plasticizer contained within the molding composition (i.e., the amount of the DOTP and any additional plasticizer). For example, when the plasticizer composition includes DOTP and the additional plasticizer, the total amount of plasticizer is the amount of DOTP and the amount of the additional plasticizer.

Suitable additional plasticizers are described above. In certain embodiments, the additional plasticizer is selected from among the adipic acid dialkyl esters with 4 to 9 carbon atoms in the alkyl group and the 2,5-furan-dicarboxylic acid esters with 4 to 10 carbon atoms in the alkyl group, with the ester groups of each ester having either the same or a different number of carbon atoms.

The total amount of plasticizer (i.e., the amount of the DOTP and any additional plasticizer) in the molding composition is typically of from about 0.5 to about 400, from about 0.5 to about 130, or from about 1 to about 35, parts by weight based on 100 parts by weight of polymer. Typically, the total amount of plasticizer is a variable that depends upon the specific polymer or polymer blend contained in the molding composition.

In certain embodiments, the polymer includes only PVC (i.e., PVC is the only polymer present in the molding composition), and the plasticizer composition consists essentially of DOTP and does not include the additional plasticizer (i.e., DOTP is the only plasticizer in the molding composition). In this embodiment, the plasticizer composition is present in an amount of from about 5 to about 300, from about 10 to about 100, or from about 30 to about 70, parts by weight based on 100 parts by weight of the polymer.

In certain embodiments, the polymer includes only PVC (i.e., PVC is the only polymer present in the molding composition), and the plasticizer composition includes both DOTP and the additional plasticizer. In this embodiment, the plasticizer composition is present in an amount of from about 1 to about 400, from about 10 to about 100, or from about 15 to about 85, parts by weight based on 100 parts by weight of the polymer.

In other embodiments, the polymer is rubber, and the plasticizer composition is present in an amount of from about 1 to about 60, from about 1 to about 40, or from about 2 to about 30, parts by weight based on 100 parts by weight of the rubber.

The molding composition may also comprise suitable additives. The additives include, but are not limited to, additives are reinforcing fillers, such as carbon black or silicon dioxide, other fillers, a methylene donor such as hexamethylenetetramine (HMT), a methylene acceptor such as a phenolic resin modified with cardanol (from cashew nuts), a vulcanizing or crosslinking agent, a vulcanizing or crosslinking accelerator, activators, various types of oil, anti-aging agents and various other additives, such as stabilizers, lubricants, fillers, pigments, flame retardants, light stabilizers, blowing agents, polymeric processing aids, impact modifiers, optical brighteners, antistatic agents, biostabilizers, and other additives that are known to be incorporated into tire and other rubber compounds.

The molding composition may also include one or more stabilizers for increasing the stability of the molding composition. Suitable stabilizers include such solid or liquid stabilizers used in PVC formulation. For example, the stabilizers include Ca/Zn, Ba/Zn, Pb or Sn stabilizers as well as acid-binding layered silicates such as hydrotalcite. The stabilizer may be present in an amount of from about 0.05 to about 7, from about 0.1 to about 5, from about 0.2 to about 4, or from about 0.5 to about 3, parts by weight based on 100 parts by weight of the molding composition.

The molding composition may also include one or more lubricants for processing plastics, for example hydrocarbons such as oils, paraffins and polyethylene waxes, fatty alcohols with 6 to 20 carbon atoms, ketones, carboxylic acids such as fatty acids and montanic acid, oxidized polyethylene wax, metal salts of carboxylic acids, carboxylic acid amides and carboxylic acid esters, for example with alcohols such as ethanol, fatty alcohols, glycerol, ethanediol and pentaerythritol, and long-chain carboxylic acids as an acid component. The lubricants are included in an amount to be effective between polymeric pellets, particularly PVC pellets, and reduce frictional forces during mixing, plasticizing and thermoforming. Specifically, the lubricants may be present in an amount of from about 0.01 to about 10, from about 0.05 to about 5, from about 0.1 to about 3, or from about 0.2 to about 2, parts by weight based on 100 parts by weight of the molding composition.

The molding composition may also include one or more fillers such as carbon black and other organic fillers, natural calcium carbonates such as chalk, limestone and marble, synthetic calcium carbonates, dolomite, silicates, silicic acid, sand, diatomaceous earth, and aluminum silicates such as kaolin, mica and feldspar. In certain embodiments, the fillers are calcium carbonates, chalk, dolomite, kaolin, silicates, talc and carbon black. In general, the fillers have a positive effect particularly on the compression, tensile and bending strength, hardness, and thermostability of the molding composition, particularly PVC molding compositions. The fillers may be present in an amount of from about 0.01 to about 80, from about 0.1 to about 60, from about 0.5 to about 50, or from about 1 to about 40, parts by weight based on 100 parts by weight of the molding composition.

The molding composition may also include one or more pigments to modify the performance and/or appearance of the molding composition. Both inorganic and organic pigments may be used. Suitable inorganic pigments are, for example, cadmium pigments such as CdS, cobalt pigments such as $CoO/Al_2O_3$, and chromium pigments such as $Cr_2O_3$. Suitable organic pigments are, for example, monoazo pigments, condensed azo pigments, azomethine pigments, anthraquinone pigments, quinacridones, phthalocyanine pigments, dioxazine pigments and aniline pigments. The pigments may be present in an amount of from about 0.01 to about 10, from about 0.05 to about 5, from about 0.1 to about 3, or from about 0.5 to about 2, parts by weight based on 100 parts by weight of the molding composition.

The molding composition may also include one or more flame retardants to reduce flammability and smoke generation during combustion. Suitable flame retardants are, for example, antimony trioxide, phosphate esters, chloroparaffin, aluminum hydroxide, boron compounds, molybdenum trioxide, ferrocene, calcium carbonate and magnesium carbonate. The flame retardants may be present in an amount of from about 0.01 to about 10, from about 0.1 to about 8, from about 0.2 to about 5, or from about 0.5 to about 2, parts by weight based on 100 parts by weight of the molding composition.

The molding composition may also include light stabilizers to protect articles manufactured from the molding composition from surface damage due to exposure to light. Examples of suitable light compounds include hydroxybenzo-phenones, hydroxyphenyl-benzotriazoles, oxalanilides, phenyltriazines, cyanoacrylates or tetramethylpiperidines ("HALS(Hindered Amine Light Stabilizers)"-amines). Typically, the light stabilizers are present in an amount of from about 0.01 to about 7, from about 0.1 to about 5, from about 0.2 to about 4, or from about 0.5 to about 3, parts by weight based on 100 parts by weight of the molding composition.

The molding composition may also include foaming agents to facilitate the manufacture of expandable molding compositions for foamed molding composition applications, like floor coverings, wall coverings and synthetic leather. Suitable foaming agents include, azodicarbonamide, oxybis-benzenesulphonylhydrazide, sodiumbicarbonate, toluenesulphonylhydrazide, para-toluenesulphonylsemicarbazide, or 5-phenyltetrazol. The foaming agents may be present in an amount of from about 0.01 to about 10, from about 0.1 to about 5, from about 0.2 to about 3, or from about 0.5 to about 1.5, parts by weight based on 100 parts by weight of the molding composition.

The molding composition may also include a kicker to catalyze the decomposition of the foaming agents in the manufacture of foamed molding compositions and molding composition applications. An example of a kicker is zinc oxide. The kicker may be present in an amount of from about 0.01 to about 10, from about 0.1 to about 5, from about 0.2 to about 3, or from about 0.3 to about 1, parts by weight based on 100 parts by weight of the molding composition. It is to be appreciated that the additives described above are examples of suitable additives and do not limit the scope of this disclosure.

The molding composition may be used for the manufacture of housings for electrical appliances, tools, pipes, cables, hoses, wire sheathing, window profiles, components for vehicle manufacture, tires, furniture, foam for upholstery and mattresses, tarpaulins, seals, composite films, recording discs, synthetic leather, packaging containers, adhesive tapes, coatings, gloves, medical products, hygiene products, food packaging, interior decoration products, toys and childcare articles, sports and leisure products, clothing, fibers for fabrics, disposable gloves, flooring coverings, sports floors, luxury vinyl tiles, cove base skirting, floor mats, traffic cones, wall coverings, foamed or non-foamed wallpapers, interior paneling, console covers in vehicles, dolls, inflatable toys, balls, action figures, modeling clay, swimming aids, baby carriage covers, changing mats, hot-water bottles, and teething rings.

The present disclosure also provides a plastisol composition comprising the plasticizer composition. The plasticizer composition is an ideal component in the plastisol composition due to the excellent gelling properties of the plasticizer composition. The plastisol composition includes both the plasticizer composition and a polymer. Suitable polymers are described in detail above. In one embodiment, the polymer is PVC such that the plastisol composition is a PVC plastisol composition.

As described above, the plasticizer composition may comprise the additional plasticizer that is different than DOTP and the di-ester according to Formula I. When the plasticizer composition includes the additional plasticizer, the additional plasticizer is typically present in an amount of from about 1 to about 90, from about 5 to about 50, or from about 10 to about 30 parts by weight based on 100 parts by weight of the total amount of plasticizer in the plastisol composition.

Although not required, when the plasticizer composition does not include an additional plasticizer (i.e., DOTP is the only plasticizer), the plasticizer composition is typically present in the plastisol composition in an amount of from about 5 to about 300, or from about 10 to about 100, parts by weight, for each 100 parts by weight of the polymer.

In other embodiments, where the plasticizer composition includes both DOTP and the additional plasticizer, the total amount of plasticizer is typically present in the plastisol composition in an amount of from about 5 to about 300, or from about 10 to about 100, parts by weight, for each 100 parts by weight of the polymer.

Plastisol compositions are typically transformed into a finished product by applying the plastisol composition and subsequently gelling the applied plastisol composition by heating and then cooling to obtain a homogeneous article. The various application processes include processes that are performed at ambient temperature such as spread coating processes, casting processes such as slush molding and rotational molding, dip coating processes, injection molding processes, etc. PVC plastisol compositions are particularly suitable for the manufacture of PVC films, seamless hollow articles and gloves, and for applications in the textile industry such as textile coatings.

The present disclosure also provides a powder coating composition comprising the plasticizer composition. The powder coating composition comprising the plasticizer composition typically has low volatility and thus a low fogging value.

A powder coating composition is a type of coating that is applied as a free-flowing, dry powder. In general, powder coating compositions are used to create a hard finish that is tougher than conventional coatings. The powder coating composition is mainly used for coating of metals, such as household appliances, aluminum extrusions, drum hardware, and automobile and bicycle parts. However, other substrates may also be used. For example, certain powder coating composition are suitable for MDF (medium-density fiberboard), and the like. The powder coating composition is typically applied electrostatically by spraying or in a fluidized bed. The applied powder coating composition is typically cured under heat to allow it to flow and form a "skin." The powder coating composition may be a thermoplastic or a thermoset powder coating composition.

In addition to the plasticizer composition, the powder coating composition also includes a polymer. The polymer is not particular limiting and may be either a thermoset and thermoplastic polymer. Examples of typical polymers include, but are not limited to, polyester, polyurethane, polyester-epoxy, epoxies (including fusion bonded epoxy), and acrylics.

In general, the production process for powder coating compositions usually includes four steps. In the first step, granules of the polymer are mixed with hardener (for thermoset polymers), pigments, the plasticizer composition, and additives. In the second step, the mixture is heated and extruded. In the third step, the extruded mixture is rolled flat, cooled and broken into small chips. Finally, in the fourth step, the chips are milled and sieved to make a fine powder.

In general, the application of the powder coating composition includes three steps, which are preparing a substrate (e.g. pretreatment, surface roughing, surface cleaning, etc.), applying the powder coating composition as described above to the substrate, and curing the powder coating composition.

It is to be appreciated that the general production process and application process of the powder coating composition is a template for producing and applying the powder coating composition. As such, a person of ordinary skill in the art may add or reduce the number of steps required to perform the respective process in order to accommodate the particular formulation and/or application of the powder coating composition. A more descriptive methodology of producing and applying the powder coating composition is described in detail in D. Bate: The Science of Powder Coatings, Volume 1 and 2, SITA Technology, London, 1990 and in M. D. Howell: The Technology, Formulation and Application of Powder Coatings, Powder Coating, Volume 1, John Wiley & Sons, 2000, which are incorporated by reference in their entirety.

Referring back to the powder coating composition, in embodiments where the plasticizer composition does not include the additional plasticizer (i.e., DOTP is the only plasticizer in the powder coating composition), the plasticizer composition is present in an amount of from about 5 to about 300 or from about 10 to about 100, parts by weight based on 100 parts by weight of the polymer.

In certain embodiments, the plasticizer composition includes both DOTP and the additional plasticizer. In these embodiments, the additional plasticizer is typically present in an amount of from about 1 to about 90, from about 5 to about 50, or from about 10 to about 30, parts by weight based on 100 parts by weight of the total amount of plasticizer. Moreover, in these embodiments, the plasticizer composition is present in an amount of from about 5 to about 400 or from about 50 to about 200, parts by weight based on 100 parts by weight of the polymer.

In certain embodiments, the molding composition is used to manufacture molded articles and films. In particular, these molded articles and/or films include housings for electrical appliances such as kitchen appliances and computer cases; tools; apparatus; pipes; cables; hoses such as plastic hoses, water hoses and irrigation hoses, industrial rubber hoses and chemical hoses; wire sheathing; window profiles; components for vehicle manufacture such as body parts and vibration dampers for engines, and tires; furniture such as chairs, tables and shelves; foam for upholstery and mattresses; tarpaulins such as truck tarpaulins and tent tarpaulins; seals; composite films such as films for laminated safety glass, especially for vehicle windows and window panes; recording discs; synthetic leather; packaging containers; adhesive tapes; coatings; and gloves.

In addition, the molding composition is suitable for the manufacture of molded articles and films that come into direct contact with people or goods that contact and/or seal editable commodities. Such molded articles and films include hygiene products, food packaging, interior decoration products, toys and childcare articles, sports and leisure products, clothing, fibers for fabrics, disposable gloves, etc.

Medical products that can be manufactured from the molding composition include, but are not limited to, enteral feeding tubes, hemodialysis tubes, respiratory tubes, infusion tubes, infusion bags, blood bags, catheters, tracheal tubes, disposable syringes, gloves and breathing masks.

Food packaging that can be manufactured from the molding composition include cling films, food hoses, drinking water hoses, containers for storing or freezing foodstuffs, lid seals, caps, bottle tops and synthetic wine corks.

Interior decoration products that can be manufactured from the molding composition include flooring coverings, which may be homogeneous or composed of several layers, including one or more foam layer, such as standard floor coverings, sports floors and luxury vinyl tiles (LVT), cove base skirting, floor mats, traffic cones, synthetic leather, wall coverings and foamed or non-foamed wallpapers in buildings, and interior paneling and console covers in vehicles.

Toys and childcare articles that can be manufactured from the molding composition in the context of the present invention include, for example, dolls, inflatable toys such as balls, action figures, modeling clay, swimming aids, baby carriage covers, changing mats, hot-water bottles, teething rings and bottles.

Sports and leisure products that can be manufactured from the molding composition include exercise balls, exercise mats, cushions, massage balls and rollers, shoes and shoe soles, balls, air mattresses and drink bottles.

Clothing that can be manufactured from the molding composition include latex clothing, protective clothing, rain jackets and gumboots, and T-shirts containing printed ink.

The present disclosure also provides an extrusion aid, a calendaring agent; a rheology modifiers; a surface-active compositions such as a melt flow enhancers, a film-forming agents, a defoamers, an antifoam, a wetting agent, a coalescing agent and an emulsifier; a lubricant such as lubricating oils, greases and pastes; a quencher for chemical reactions; a phlegmatizer; a pharmaceutical product; an adhesive; an impact modifier and an extender; and/or a heat transfer oil (e.g. in refrigerators), comprising the plasticizer composition.

The present disclosure also provides a method for preparing an aromatic di-ester. The method includes combining an aromatic di-acid and a linear or branched C4-C13 alcohol to form a mixture. Typically, the mixture is combined inside of a reactor. The method also includes heating the mixture from a first temperature (T1) to a second temperature (T2) without a catalyst present in the mixture. In other words, the catalyst is not present in the mixture while the mixture is being heated from the first temperature (T1) to the second temperature (T2). The mixture may be heated by any suitable means, such as heating the reactor using natural gas burners or with internal heating coils.

The method further includes combining a titanium catalyst with the mixture after the mixture is at the second temperature (T2). The method further includes increasing pressure from a first pressure (P1) to a second pressure (P2) after the mixture is at the second temperature (T2). The method further includes increasing the temperature from the second temperature (T2) to a third temperature (T3) while maintaining the second pressure (P2).

In certain embodiments, the aromatic di-acid is phthalic acid, isophthalic acid, and/or terephthalic acid. Typically, the aromatic di-acid is terephthalic acid. Although not required, in certain embodiments, the C4-C13 alcohol is n-butanol, isobutanol, n-pentanol, isopentanol, n-hexanol, 2-ethylhexanol, isohexanol, n-heptanol, isoheptanol, n-octanol, isooctanol, n-nonanol, isononanol, n-decanol, isodecanol, n-undecanol, isoundecanol, n-dodecanol, isododecanol, n-tridecanol and isotridecanol. Typically, the C4-C13 alcohol is 2-ethylhexanol. In one embodiment, terephthalic acid and 2-ethylhexanol are combined to form the mixture.

Without being held to any particular theory, it is believed that the specific strategic sequence of temperature changes, pressure control, and timing of the catalyst addition prevents or reduces the decomposition of the C4-C13 alcohol. Preventing the decomposition of the C4-C13 alcohol is advantageous because if the alcohol was to decompose into decomposition products, the decomposition products could react with the aromatic di-acid to produce the byproducts/impurities. Moreover, it is also believed that the specific strategic sequence of temperature changes, pressure control, and timing of the catalyst addition also prevents or reduces the decomposition of the catalyst. Preventing the decomposition of the catalyst is also advantageous because the decomposition product of the catalyst may also participate in the reaction scheme and form undesirable byproducts/impurities. Hereinafter both the impurities arising from the decomposition of the C4-C13 alcohol and the impurities arising from the aromatic di-acid are collectively referred to as the "the byproduct impurities." In general, these byproduct impurities are not capable of being removed by the conventional separation techniques such as washing, distilling, and filtering. As such, avoiding the formation of the byproduct impurities is essential, because once the byproduct impurities are formed the byproduct impurities will generally be inseparable from the aromatic di-ester.

In certain embodiments, the first temperature (T1) is from about 20 to about 22° C. In other words, in these embodiments, the first temperature (T1) is about room temperature. In certain embodiments, the second temperature (T2) is from about 175 to about 185, from about 177 to about 183, or about 180, ° C. As such, in certain embodiments where the first temperature (T1) is from about 20 to about 22° C. and the second temperature (T2) is from about 175 to about 185° C., the mixture is heated from about room temperature to about 175 to about 185° C. It is believed that as the mixture is heated from the first temperature (T1) to the second temperature (T2) the lack of the catalyst prevents or reduces the decomposition of the C4-C13 alcohol, and consequently the byproduct impurities are not formed.

In certain embodiments, the third temperature (T3) is from about 210 to about 240° C. As such, in embodiments where the first temperature (T1) is from about 20 to about 22° C., the second temperature (T2) is from about 175 to about 185° C., and the third temperature (T3) is from about 210 to about 240° C., the mixture is heated from about room temperature to about 175 to about 185° C., the catalyst is then added and the mixture is heated to about 210 to about 240° C. It is believed that adding the catalyst after the second temperature (T2) is advantageous in avoiding or reducing the byproduct impurities because after the temperature reaches the second temperature (T2) and the pressure is raised from the first pressure (P1) to the second pressure (P2), the amount of time that the C4-C13 alcohol and catalyst are exposed to the pressure, and each other (i.e., the amount of time that the C4-C13 alcohol and catalyst are exposed to one another) prevents or reduces the byproduct impurities.

In certain embodiments, the method further includes the step of preventing pressure from increasing from the first pressure (P1) as the temperature is increased from the first temperature (T1) to the second temperature (T2). Although the method is not limited to any particular mechanism for preventing pressure from forming, one example of a suitable mechanism includes performing the reaction in a reactor that is equipped with a vent, and opening and leaving the vent in an open position while the mixture is heated from the first temperature (T1) to the second temperature (T2). The vent, while in the open position, prevents any pressure from forming in the reactor such that the reactor operates at the first pressure, rather than an elevated or decreased pressure, so long as the vent is in the open position. It is believed that preventing pressure from increasing while the mixture is heated from the first temperature (T1) to the second temperature (T2) is advantageous because maintaining the first pressure (P1) reduces or eliminates the byproduct impurities. In other words, maintaining the first pressure (P1) reduces the decomposition of 2-ethylhexanol and the catalyst such that the byproduct impurities are not formed. In certain embodiments, the first pressure (P1) is atmospheric pressure (i.e., approximately 1 atm). In certain embodiments, the second pressure (P2) is from about 1.3 to about 1.6, or about 1.4 to about 1.5, atm. In certain embodiments, the first pressure (P1) is atmospheric pressure and the second pressure (P2) is from about 1.3 to about 1.6 atm.

In certain embodiments, the method further includes the step of adding an aqueous solution of sodium hydroxide to neutralize any remaining carboxylic acid groups on the aromatic di-acid (or acid monoester if the aromatic di-acid has reacted with one mole of the C4-C13 alcohol) and forms a salt with the titanium catalyst. In embodiments where the aromatic di-acid is terephthalic acid, the aqueous solution of sodium hydroxide neutralizes the any remaining carboxylic acid groups on the terephthalic acid and forms a salt with the titanium catalyst. Once the mixture is neutralized, the titanium catalyst salt can be removed by filtering and the neutralized aromatic di-acid can be removed by decanting the aqueous solution. It is to be appreciated that neither the neutralized aromatic di-acid nor the titanium catalyst salt is the byproduct impurity, as the byproduct impurities are not capable of being isolated (i.e., separated from the aromatic di-ester) via traditional separation techniques such as filtering and/or decanting.

The method may further comprise the step of distilling to remove the C4-C13 alcohol. In embodiments where the C4-C13 alcohol is 2-ethylhexanol, the method includes the step of distilling to remove 2-ethylhexanol. The distilling step may also remove water, if present. The step of distilling is typically complete when the concentration of 2-ethylhexanol and water is below 1000 ppm. In certain embodiments, the method may further comprise the step of removing water. Removing water is advantageous because the removal of water "pushes" the reaction equilibrium towards the formation of the aromatic di-ester. Typically when the method includes the step of removing water, the water is removed while the temperature is at or above the second temperature (T2). It should be appreciated that although residual water could be removed during distilling, the step of removing water is a separate step from the step of distilling. Typically, the step of distilling is performed after the reaction is complete to remove the residual 2-ethylhexanol and the step of removing water is preformed while the reaction is proceeding to push the reaction. Although the method is not limited to any particular means for removing water, one example of a suitable means includes mounting a water removal tower to the reactor.

The method may further comprise the step of decreasing the pressure to a third pressure (P3) that is less than the first pressure (P1) after the pressure has reached the second pressure (P2) and while the temperature is at the third temperature (T3). Decreasing the pressure to the third pressure (P3) generally aids in the removal of water and thus further pushes the reaction equilibrium towards the formation of the aromatic di-ester. Although not required, the third pressure (P3) is typically from about 0.2 to about 0.6 atm. When the third pressure (P3) is from about 0.2 to about 0.6 atm, the pressure generally aids in the removal of water because the third pressure (P3) is below atmospheric pressure and water molecules are generally more extractable at pressures below atmospheric pressure. Typically, the third pressure (P3) is achieved by introducing a vacuum.

In certain embodiments, the step of maintaining the second pressure (P2) as the temperature is increased from the second temperature (T2) to the third temperature (T3) includes introducing a vacuum, and may further include releasing an inert gas. It is to be appreciated that releasing an inert gas may be accomplished by various methods which includes, but is not limited to, opening a value to release nitrogen. Introducing a vacuum releases pressure to prevent the pressure from exceeding the second pressure (P2), while releasing (i.e., pumping in) an inert gas increases the pressure. In certain instances, the vacuum may be introduced to maintain pressure while the inert gas may be simultaneously released to further maintain pressure, even though the respective actions when viewed in isolation may appear diametrically opposed. As such, when the method includes introducing a vacuum and releasing an inert gas, each event cooperates with the other for maintaining the second pressure (P2).

The plasticizer composition which comprises DOTP, and which is substantially free of the di-ester according to Formula I may be prepared by an embodiment of the above method. The method includes the step of combining terephthalic acid and 2-ethylhexanol to form a mixture, heating the mixture from a first temperature (T1) to a second temperature (T2) without a catalyst present in the mixture, combining a titanium catalyst with the mixture after the mixture is at the second temperature (T2), increasing pressure from a first pressure (P1) to a second pressure (P2) after the mixture is at the second temperature (T2); and increasing the temperature from the second temperature (T2) to a third temperature (T3) while maintaining the second pressure (P2). Although not required, the first, second, and third temperatures (T1), (T2), (T3), and the first and second pressures (P1), (P2) may be the ranges defined above in the method of preparing the aromatic di-ester. In certain embodiments, at least one of the first, second, and third temperatures (T1), (T2), (T3), and the first and second pressures (P1), (P2) are the same ranges defined above in the method for preparing the aromatic di-ester. In other embodiments, the each of the first, second, and third temperatures (T1), (T2), (T3), and the first and second pressure (P1), (P2) are the same ranges defined above in the method for preparing the aromatic di-ester described above. As such, in certain embodiments, the first temperature (T1) is from about 20 to about 22° C., the second temperature (T2) is from about 175 to about 185° C., the third temperature (T3) is from about 210 to about 240° C., the first pressure (P1) is about atmospheric pressure, and the second pressure (P2) is from about 1.3 to about 1.6 atm.

The method for preparing the plasticizer composition comprising DOTP, and which is substantially free of the di-ester according to Formula I may further comprise the step of preventing pressure from increasing from the first pressure (P1) as the mixture is heated from the first temperature (T1) to the second temperature (T2).

The method for preparing the plasticizer composition comprising DOTP, and which is substantially free of the di-ester according to Formula I may further comprise the step of preventing pressure from increasing from the first pressure (P1) as the temperature is increased from the first temperature (T1) to the second temperature (T2).

The method for preparing the plasticizer composition comprising DOTP, and which is substantially free of the di-ester according to Formula I may further comprise the steps of adding the aqueous solution of sodium hydroxide to neutralize any remaining carboxylic acid groups on the terephthalic acid and form a titanium catalyst salt, removing the aqueous solution, distilling to remove excess 2-ethylhexanol, and filtering.

It is to be appreciated that the specific strategic sequence of temperature changes, pressure control, and timing of the catalyst addition prevents or reduces the decomposition of the 2-ethylhexanol and/or the titanium catalyst. Preventing the decomposition of the 2-ethylhexanol and/or the titanium catalyst is advantageous because if the decomposition was to occur, the decomposition products could react with the terephthalic acid to produce the di-ester according to Formula I. As described above, the di-ester according to Formula I are not capable of being removed by the conventional separation techniques such as washing, distilling, and filtering. As such, avoiding the formation of the di-ester according to Formula I is essential, because once the at least di-ester according to Formula I is formed the at least di-ester is inseparable from DOTP. In addition, preventing the decomposition of the 2-ethylhexanol and/or the titanium catalyst is advantageous because if the decomposition was to occur, the decomposition products could react with the terephthalic acid to produce the reaction product of (1) terephthalic acid, and (2) decomposition products of 2-ethylhexanol, decomposition products of titanium catalysts, or combinations thereof. Moreover, the decomposition products could also react with the terephthalic acid to produce DMT. As such, in certain embodiments, the method for preparing the plasticizer composition which comprises DOTP is substantially free of (1) the di-ester according to Formula I, (2) DMT, and (3) the reaction product of (i) terephthalic acid, and (ii) decomposition products of 2-ethylhexanol, decomposition products of titanium catalysts, or combinations thereof.

In certain embodiments, the plasticizer composition prepared as described above includes DOTP in an amount greater than or equal to 99.9 parts by weight based on 100 parts by weight of the plasticizer composition, and the plasticizer composition includes less than 0.1 parts by weight of the di-ester according to Formula I, based on 100 parts by weight of the plasticizer composition.

In certain embodiments, the plasticizer composition prepared as described above includes DOTP in an amount greater than or equal to 99.95 parts by weight based on 100 parts by weight of the plasticizer composition, and the plasticizer composition includes less than 0.05 parts by weight of the di-ester according to Formula I, based on 100 parts by weight of the plasticizer composition.

In certain embodiments, the plasticizer composition prepared as described above includes DOTP in an amount greater than or equal to 99.97 parts by weight based on 100 parts by weight of the plasticizer composition, and the plasticizer composition includes less than 0.03 parts by weight of the di-ester according to Formula I, based on 100 parts by weight of the plasticizer composition.

In certain embodiments, the plasticizer composition prepared as described above is also substantially free of the reaction product of (1) terephthalic acid, and (2) decomposition products of 2-ethylhexanol, decomposition products of titanium catalysts, or combinations thereof and substantially free of DMT.

EXAMPLES

Example 1, which is an embodiment of the plasticizer composition of this disclosure, is prepared in a reactor having a vent and a water removal column mounted to the reactor. The vent has an open and closed position. When the vent is in the open position (i.e., the vent is open), pressure is not formed in the reactor. As such, the reactor is maintained at atmospheric pressure. 2-ethylhexanol is pumped into the reactor and agitated. Terephthalic acid, in the form of a solid, is added to the reactor. No components other than 2-ethylhexanol and terephthalic acid are added to the reactor. The reactor is heated to approximately 180° C. using natural gas burners located beneath the reactor and with 8 bar steam through an internal heating coil in the reactor. The vent on the reactor is in the open position prior to the heating of the reactor. The vent continues to stay in the open position as the reactor is heated to 180° C. The vent, while in the open position, prevents any pressure from forming in the reactor such that the reactor operates at atmospheric pressure. No measurable amount of reaction occurs between the 2-ethylhexanol and the terephthalic acid while the reactor is heated to 180° C. Once the reactor reaches 180° C., the reaction between 2-ethylhexanol and terephthalic acid begins. The water is continuously removed from the reactor through the water removal tower.

After the reaction reaches 180° C., a titanium catalyst is added and the vent is closed. After the vent is closed, nitrogen gas is continuously pumped into the reactor to increase the reaction pressure from 1 atm (atmospheric pressure) to 1.4 atm. The process of pumping nitrogen gas into the reactor lasts for the duration of the reaction. The reaction pressure is maintained at 1.4 atm. After the catalyst is added and the pressure reaches 1.4 atm, the temperature in the reactor is increased from 180° C. to 220° C. A vacuum is introduced (i.e., pulled) to prevent any pressure over 1.4 atm.

As the 2-ethylhexanol and terephthalic acid reaction proceeds, water is continuously removed from the reactor. As the reaction nears completion, the vacuum is increased to lower the reaction pressure to 0.4 atm to form the plasticizer composition.

The plasticizer composition has an acid number that is less than 0.07 mg KOH. The plasticizer composition is then washed with an aqueous solution of sodium hydroxide, distilled, and filtered.

Comparative Example A is di(2-ethylhexyl)terephthalate Eastman 168®, supplied by Eastman Chemical Company, Kingsport, Tenn., US.

The properties of the plasticizer composition of Example 1 and Comparative Example A are compared in Table 1.

TABLE 1

| | Example 1 | Comparative Example A |
|---|---|---|
| DOTP Content, % | 99.9 | 97.94 |
| MOTP Content, % | <0.02 | 2.04 |
| 2-ethylhexanol content, ppm | 20 | 20 |
| Density, 25/25C, g/cm3 | 0.9779 | 0.9793 |
| Density, 20/20C, g/cm3 | 0.9818 | 0.9833 |
| Acid Number, mg KOH/gm | 0.007 | 0.012 |
| Water, wt. % | 0.03 | 0.02 |
| Color, Pt—Co units (APHA) | 10 | 3 |
| Volatility at 110 C. for 1 hr (EPA24, ASTM D2369), % | 0.50 | 0.54 |
| Volatility at 130 C. for 1 hr, % | 1.32 | 1.52 |
| Volatility at 150 C. for 1 hr, % | 2.83 | 5.60 |
| Fog, mg | 1.38 | 3.50 |

Example 1 is substantially free of methyl (2-ethylhexyl) terephthalate (MOTP) (i.e., the concentration of is less than <0.02%). Conversely, comparative Example A includes 2.04% MOTP. The influential presence of MOTP is believed to be principally responsible for the disparity in the volatility and fogging values. Specifically, in regards to volatility, Example 1 after 1 hour at 150° C. was only 2.83% compared with 5.60% for Comparative Example A. Likewise, the fogging value was only 1.38 mg for Example 1 compared to 3.50 mg for Comparative Example A.

To evaluate the plasticizing properties in thermoplastic processing of the Example 1 and Comparative Example A, 0.5-mm-thick plasticized PVC sheets were fabricated using Example 1 and Comparative Example A, at 40, 50, and 70, parts by weight each based on 100 parts by weight of PVC. The sheets were made by rolling and pressing plasticized PVC.

To eliminate the effects of using different additives, 6 plasticized PVC sheets were made. The amount of PVC and stabilizer present in the PVC is expressed in parts by weight based on 100 parts by weight of the PVC sheet. The amount of Example 1 AND Comparative Example A present in the PVC sheet is expressed in parts by weight based on 100 parts by weight of PVC. The PVC sheet formulations are as follows:

| Component | Amount |
|---|---|
| PVC (Oxyvinyls 226F1) | 100 |
| Example 1 or Comparative Example A | 40, 50 and 70 |
| Stabilizer (Baerlocher 17602) | 3 |

The PVC is a homopolymer supplied by Oxyvinyls, Los Angeles, Calif.

The stabilizer is a liquid Ba—Zn stabilizer supplied by Baerlocher, Lingen, Germany.

The components were mixed in a Hobart mixer at room temperature. The mixture was subsequently plastified on an electrically heated laboratory roll mill (Labtech Type "150") and rolled out to a rough sheet. The roll speeds were 20 rpm (front roll) and 24 rpm (back roll), the rolling time was 5 minutes and the temperatures were as follows:

| Amount of plasticizer composition | Front roll | Back roll |
|---|---|---|
| 40 | 340° F. | 335° F. |
| 50 | 335° F. | 330° F. |
| 70 | 320° F. | 315° F. |

The resulting rolled sheet was then pressed at a pressure of 25,000 psi (on bore 5") and a temperature of 350° F. for 5 minutes and then a further 5 minutes at the same pressure while cooling to below 120° F. The sheets were then pressed on a Wabash Genesis Series Hydraulic Compression Press Model G30H/30C-X to a plasticized PVC sheet with a thickness of 20 or 70 mils, according to the measurements to be performed. Application tests were performed on the resulting rolled, pressed sheets.

The application tests were carried out by standard methods and the results are summarized in Table 2.

TABLE 2

| Property | Method | Example 1 70 | Comparative Example A 70 | Example 1 50 | Comparative Example A 50 | Example 1 40 | Comparative Example A 40 |
|---|---|---|---|---|---|---|---|
| Durometer Shore A Hardness, instant | D-2240 | 75.8 | 76.2 | 87.7 | 87.1 | 92.6 | 92.4 |
| Durometer Shore A Hardness, 15 s | D-2240 | 69.3 | 69.6 | 82.2 | 81.8 | 88.6 | 88.6 |
| Brittleness, Tb, C. | D-746 | −43 | −43 | −32 | −32 | −23 | −22 |
| Water Extraction, 24 hrs at 70 C., wt % | SPI-VD-T12 | 0.1 | 0.1 | 0.1 | 0.1 | 0.1 | 0.1 |
| Volatility, 24 hrs at 100 C., wt % | D-1203 | 1.8 | 2.6 | 1.6 | 2.2 | 1.6 | 2.1 |

Table 2 illustrates that Example 1 and Comparative Example A have similar mechanical properties as measured by the Shore A hardness, similar low-temperature flexibility properties as measured by the brittleness temperature, and similar resistance to water as measured by the water extraction.

However, with a plasticizer content of 70 the PVC sheet produced with Example 1 has a much lower volatility (1.8%) than the PVC sheet produced with Comparative Example A (2.6%).

Many modifications and variations of the present disclosure are possible in light of the above teachings, and the disclosure may be practiced otherwise than as specifically described within the scope of the appended claims. The subject matter of all combinations of independent and dependent claims, both single and multiple dependent, is herein expressly contemplated. It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention claimed is:

1. A plasticizer composition comprising di(2-ethylhexyl) terephthalate and which is substantially free of a di-ester according to Formula I:

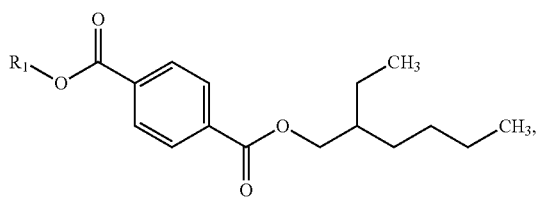

Formula I wherein R1 is a straight-chain or branched alkyl group having from 1 to 13 carbon atoms;
wherein R1 is different than 2-ethylhexane; and
wherein said di(2-ethylhexyl) terephthalate is present in an amount greater than or equal to 99.9 parts by weight based on 100 parts by weight of said plasticizer composition and said di-ester according to Formula I is present in an amount less than 0.1 parts by weight based on 100 parts by weight of said plasticizer composition.

2. The plasticizer composition as set forth in claim 1 wherein said di(2-ethylhexyl) terephthalate is present in an amount greater than or equal to 99.95 parts by weight based on 100 parts by weight of said plasticizer composition, and said di-ester according to Formula I is present in an amount less than 0.05 parts by weight based on 100 parts by weight of said plasticizer composition.

3. The plasticizer composition as set forth in claim 2 wherein said di(2-ethylhexyl) terephthalate is present in an amount greater than or equal to 99.97 parts by weight based on 100 parts by weight of said plasticizer composition, and said di-ester according to Formula I is present in an amount less than 0.03 parts by weight based on 100 parts by weight of said plasticizer composition.

4. The plasticizer composition as set forth in claim 1 wherein said di-ester according to Formula I comprises methyl (2-ethylhexyl) terephthalate.

5. The plasticizer composition as set forth in claim 1 wherein said plasticizer composition is also substantially free of the reaction product of:
   i. terephthalic acid; and
   ii. decomposition products of 2-ethylhexanol, decomposition products of a titanium catalysts, or combinations thereof.

6. The plasticizer composition as set forth in claim 5 wherein said plasticizer composition is also substantially free of di(methyl) terephthalate.

7. The plasticizer composition as set forth in claim 1 wherein said plasticizer composition further comprises one or more ester that is different from said di(2-ethylhexyl) terephthalate; and said one or more ester is selected from a group consisting of cyclohexanedicarboxylic acid esters, phthalic acid dialkyl esters, phthalic acid alkylaralkyl esters, terephthalic acid dialkyl esters different from said di-ester in accordance with Formula I and said di(methyl) terephthalate, trimellitic acid trialkyl esters, adipic acid dialkyl esters, benzoic acid alkyl esters, dibenzoic acid esters of glycols, hydroxybenzoic acid esters, esters of saturated monocarboxylic acids and dicarboxylic acids, esters of unsaturated dicarboxylic acids, amides and esters of aromatic sulfonic acids, alkylsulfonic acid esters, glycerol esters, isosorbide esters, phosphoric acid esters, citric acid triesters, alkylpyrrolidone derivatives, 2,5-furandicarboxylic acid esters, 2,5-tetrahydrofurandicarboxylic acid esters, epoxidized vegetable oils based on triglycerides and saturated or unsaturated fatty acids, and polyesters of aliphatic and aromatic polycarboxylic acids with polyhydric alcohols.

8. A plastisol composition comprising said plasticizer composition as set forth in claim 1.

9. A powder coating composition comprising said plasticizer composition as set forth in claim 1.

10. An extrusion aid composition, a calendaring agent composition, a rheology modifier composition, a surface-active composition, a melt flow enhancer composition, a film-forming agent composition, a defoamer composition, an antifoamer composition, a wetting agent composition, a coalescing agent composition, an emulsifier composition, a lubricant composition, a lubricating oil composition, a lubricating grease composition, a quenchers for a chemical reaction, a phlegmatizer composition, a pharmaceutical composition, an adhesive composition, an impact modifier composition, an extender composition, or a heat transfer oil composition comprising said plasticizer composition as set forth in claim 1.

11. A plasticizer composition comprising;
di(2-ethylhexyl) terephthalate present in an amount greater than or equal to 99.9 parts by weight based on 100 parts by weight of said plasticizer composition;
wherein said plasticizer composition comprises less than a combined total of 0.1 parts by weight based on 100 parts by weight of said plasticizer composition, of the following:
   i. a di-ester according to Formula I:

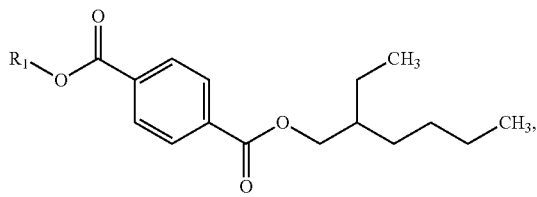

Formula I wherein $R_1$ is a straight chain or branched alkyl group having from 1 to 13 carbon atoms, and
   wherein $R_1$ is different than 2-ethylhexane;
   ii. the reaction product of:
      a. terephthalic acid, and
      b. decomposition products of 2-ethylhexanol, decomposition products of a titanium catalyst, or combinations thereof; and
   iii. di(methyl) terephthalate.

12. A plasticizer composition comprising di(2-ethylhexyl) terephthalate which is substantially free of a di-ester according to Formula I:

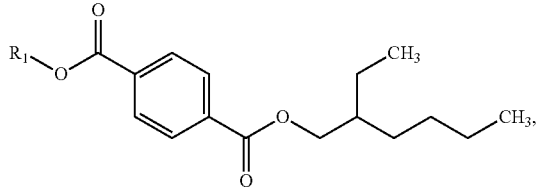

Formula I $R_1$ is a straight-chain or branched alkyl group having from 1 to 13 carbon atoms and $R_1$ is different than 2-ethylhexane;
wherein said plasticizer composition is prepared by a method comprising the steps of:
   combining terephthalic acid and 2-ethylhexanol to firm a mixture;
   heating the mixture from a first temperature (T1) to a second temperature (T2) without a catalyst present in the mixture;
   combining a titanium catalyst with the mixture after the mixture is at the second temperature (T2);
   increasing pressure from a first pressure (P1) to a second pressure (P2) after the mixture is at the second temperature (T2); and
   increasing the temperature of the mixture from the second temperature (T2) to a third temperature (T3) while maintaining the second pressure (P2);
wherein said di(2-ethylhexyl) terephthalate is present in an amount greater than or equal to 99.9 parts by weight based on 100 parts by weight of said plasticizer composition and said di-ester according to Formula I is present in an amount less than 0.1 parts by weight based on 100 parts by weight of said plasticizer composition.

13. The plasticizer composition as set forth in claim 12 wherein the second temperature (T2) is from about 175 to about 185° C.

14. The plasticizer composition as set forth in claim 13 wherein the third temperature (T3) is from about 210 to about 240° C.

15. The plasticizer composition as set forth in claim 12 wherein the method further comprises the step of preventing pressure from increasing from the first pressure (P1) as the temperature is increased from the first temperature (T1) to the second temperature (T2).

16. The plasticizer composition as set forth in claim 12 wherein the first pressure (P1) is about atmospheric pressure.

17. The plasticizer composition as set forth in claim 16 wherein the second pressure (P2) is from about 11.3 to about 1.6 atm.

18. The plasticizer composition as set forth in claim 12 wherein the method further comprises:
    adding the aqueous solution of sodium hydroxide to neutralize any remaining carboxylic acid groups on the terephthalic acid and form a salt with the titanium catalyst;
    removing the aqueous solution;
    distilling to remove excess 2-ethylhexanol; and
    filtering.

19. The plasticizer composition as set forth in claim 18 wherein di(2-ethylhexyl) terephthalate is present in an amount greater than or equal to 99.9 parts by weight based on 100 parts by weight of the plasticizer composition, and the plasticizer composition comprises less than 0.1 parts by weight of the di-ester according to Formula I, based on 100 parts by weight of the plasticizer composition.

20. The plasticizer composition as set forth in claim 19 wherein di(2-ethylhexyl) terephthalate is present in an amount greater than or equal to 99.95 parts by weight based on 100 parts by weight of the plasticizer composition, and the plasticizer composition comprises less than 0.05 parts by weight of the di-ester according to Formula I, based on 100 parts by weight of the plasticizer composition.

21. The plasticizer composition as set forth in claim 20 wherein di(2-ethylhexyl) terephthalate is present in an amount greater than or equal to 99.97 parts by weight based on 100 parts by weight of the plasticizer composition, and the plasticizer composition comprises less than a combined total of 0.03 parts by weight of the di-ester according to Formula I, based on 100 parts by weight of the plasticizer composition.

22. The plasticizer composition as set forth in claim 12 wherein the plasticizer composition is also substantially free of:
    i. the reaction product of:
        a. terephthalic acid, and
        b. decomposition products of 2-ethylhexanol, decomposition products of the titanium catalyst, or combinations thereof; and
    ii. di(methyl) terephthalate.

23. A molding composition comprising said plasticizer composition as set forth in claim 1.

24. The molding composition as set forth in claim 23 further comprising one or more polymer selected from the group consisting of homopolymers and copolymers of:
    a reaction product of one or more C2-C10 monoolefin, 1,3-butadiene, 2-chloro-1,3-butadiene, C2-C10 alkyl esters of vinyl alcohol, vinyl chloride, vinylidene chloride, vinylidene fluoride, tetrafluoroethylene, glycidyl acrylate, glycidyl methacrylate, acrylates and methacrylates with alcohol components of branched and unbranched C1-C10 alcohols, vinyl aromatic compounds, polystyrene, (meth)acrylonitrile, ethylenic unsaturated monocarboxylic acids, ethylenic unsaturated dicarboxylic acids, maleic anhydride, vinyl acetals, polyvinyl esters, polycarbonates, polyesters, polyalkylene terephthalates, polyhydroxyalkanoates, polybutylene succinates, polybutylene succinate adipates, polyethers, polyamides, polyacrylonitrile, polymethyl methacrylates, polyvinylidene chloride, polystyrene, polyether ketones, polyurethane, thermoplastic polyurethanes, polysulfides, polysulfones, and polyphenylene ether.

25. The molding composition as set forth in claim 24 wherein said polymer is polyvinyl chloride.

26. The molding composition as set forth claim 24 wherein said plasticizer composition is present in an amount of from about 1 to about 400 parts by weight based on 100 parts by weight of said polymer.

27. The molding composition as set forth in claim 24 wherein said plasticizer composition is present in an amount of from about 5 to about 300 parts by weight based on 100 parts by weight of said polymer.

28. A method for preparing a plasticizer composition comprising di(2-ethylhexyl) terephthalate which is substantially free of a di-ester according to Formula I:

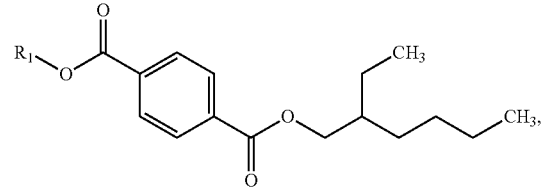

Formula I $R_1$ is a straight-chain or branched alkyl group having from 1 to 13 carbon atoms and $R_1$ is different than 2-ethylhexane, said method comprising:
    combining terephthalic acid and 2-ethylhexanol to form a mixture;
    heating the mixture from a first temperature (T1) to a second temperature (T2) without a catalyst present in the mixture;
    combining a titanium catalyst with the mixture after the mixture is at the second temperature (T2);
    increasing pressure from a first press (P1) to a second pressure (P2) after the mixture is at the second temperature (T2); and
    increasing the temperature of the mixture from the second temperature (T2) to a third temperature (T3) while maintaining the second pressure (P2);
    wherein di(2-ethylhexyl) terephthalate is present in an amount greater than or equal to 99.9 parts by weight based on 100 parts by weight of the plasticizer composition and the di-ester according to Formula I is present in an amount less than 0.1 parts by weight based on 100 parts by weight of the plasticizer composition.

29. The method as set forth in claim 28 wherein the first temperature (T1) is from about 20 to about 22° C.

30. The method as set forth in claim 29 wherein the second temperature (T2) is from about 175 to about 185° C.

31. The method as set forth in claim 30 wherein the third temperature (T3) is from about 210 to about 240° C.

32. The method as set forth in claim 28 wherein said method further comprises the step of preventing pressure from increasing from the first pressure (P1) as the temperature is increased from the first temperature (T1) to the second temperature (T2).

33. The method as set forth in claim 28 wherein the first pressure (P1) is about atmospheric pressure.

34. The method as set forth in claim 33 wherein the second pressure (P2) is from about 1.3 to about 1.6 atm.

35. The method as set forth in claim 28 wherein the mixture is formed from terephthalic acid and excess 2-ethylhexanol.

36. The method as set forth in claim 35 further comprising the step of distilling to remove 2-ethylhexanol.

37. The method as set forth in claim 28 further comprising the step of adding an aqueous solution of sodium hydroxide to neutralize any remaining carboxylic acid groups on the aromatic di-acid and form a titanium catalyst salt.

38. The method as set forth in claim 37 further comprising the step of filtering.

39. The method as set forth in claim 38 further comprising the step of removing water.

40. The method as set forth in claim 28 further comprising the step of decreasing the pressure to a third pressure (P3) that is less than the first pressure (P1) after the pressure has reached the second pressure (P2) and while the temperature is at the third temperature (T3).

41. The method as set forth in claim 40 wherein the third pressure (P3) is from about 0.2 to about 0.6 atm.

42. The method as set forth in claim 28 wherein the second pressure (P2) is maintained by introducing a vacuum.

43. The method as set forth in claim 42 wherein the second pressure (P2) is further maintained by releasing an inert gas.

44. A food wrap comprising;
polyvinylchloride; and
a plasticizer composition comprising di(2-ethylhexyl) terephthalate and which is substantially free of a di-ester according to Formula I:

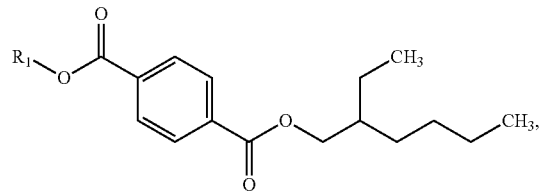

Formula I wherein $R_1$ is a straight-chain or branched alkyl group having from 1 to 13 carbon atoms, and
wherein $R_1$ is different than 2-ethylhexane,
wherein said di(2-ethylhexyl) terephthalate is present in an amount greater than or equal to 99.9 parts by weight based on 100 parts by weight of said plasticizer composition and said di-ester according to Formula I is present in an amount less than 0.1 parts by weight based on 100 parts by weight of said plasticizer composition.

* * * * *